United States Patent
Sanders

(10) Patent No.: US 10,064,703 B1
(45) Date of Patent: Sep. 4, 2018

(54) ANATOMICAL ADAPTABLE DRAPE DEVICE

(71) Applicant: MAVRIK DENTAL SYSTEMS, LTD., Ra'anana (IL)

(72) Inventor: Daniel Sanders, Ra'anana (IL)

(73) Assignee: MAVRIK DENTAL SYSTEMS, LTD., Ra'anana (IL)

( * ) Notice: Subject to any disclaimer, the term of this patent is extended or adjusted under 35 U.S.C. 154(b) by 23 days.

(21) Appl. No.: 15/434,294

(22) Filed: Feb. 16, 2017

(51) Int. Cl.
| | |
|---|---|
| *A61C 5/82* | (2017.01) |
| *A61B 46/00* | (2016.01) |
| *A61B 46/20* | (2016.01) |
| *A61C 13/15* | (2006.01) |
| *A61C 19/06* | (2006.01) |

(52) U.S. Cl.
CPC ............... *A61C 5/82* (2017.02); *A61B 46/20* (2016.02); *A61B 46/40* (2016.02); *A61C 19/003* (2013.01); *A61C 19/066* (2013.01); *A61C 2201/00* (2013.01)

(58) Field of Classification Search
CPC ............ A61C 5/82; A61C 5/90; A61C 19/066
See application file for complete search history.

(56) References Cited

U.S. PATENT DOCUMENTS

| | | | |
|---|---|---|---|
| 2,937,445 A | 5/1960 | Erickson | |
| 3,049,806 A | 8/1962 | Cofresi | |
| 3,481,329 A | 12/1969 | Warren | |
| 3,489,141 A | 1/1970 | Warren | |
| 3,527,218 A | 9/1970 | Westine | |
| 3,527,219 A | 9/1970 | Greenberg | |
| 3,536,069 A | 9/1970 | Gores | |
| 3,566,869 A | 3/1971 | Crowson | |
| 3,669,101 A | 6/1972 | Kleiner | |
| 3,731,675 A | 5/1973 | Kelly | |
| 3,742,942 A | 7/1973 | Westline | |
| 3,772,790 A | 11/1973 | Swan-Gett et al. | |
| 3,840,992 A | 10/1974 | English | |
| 4,059,101 A | 11/1977 | Richmond | |

(Continued)

FOREIGN PATENT DOCUMENTS

| | | |
|---|---|---|
| CN | 1225810 A | 8/1999 |
| DE | 871818 C | 3/1953 |

(Continued)

OTHER PUBLICATIONS

Office Action from the United Kingdom Patent Office, Application No. GB1400767.8 dated Aug. 6, 2014.

(Continued)

*Primary Examiner* — Ralph Lewis
(74) *Attorney, Agent, or Firm* — The Dobrusin Law Firm, P.C.

(57) ABSTRACT

An anatomical drape (1*a* or 1*b*), such as a dental drape, for covering a treatment area of an anatomical part, the drape comprising an elastomeric material capable of conforming to the contours of the anatomical part and including a curing agent (9) contained within internal channels distributed in the drape; and wherein activation of the curing agent, for example by a light source, causes hardening of the material to at least partially set the drape in a configuration conforming to the anatomical part. The semi-rigid set drape is liquid impermeable but gas permeable. A method of manufacturing the drape is also disclosed.

19 Claims, 11 Drawing Sheets

(56) References Cited

U.S. PATENT DOCUMENTS

| | | | |
|---|---|---|---|
| 4,106,501 A | 8/1978 | Ozbey et al. |
| 4,138,814 A | 2/1979 | Weitzman |
| 4,164,940 A | 8/1979 | Quinby |
| 4,192,071 A | 3/1980 | Erickson |
| 4,560,351 A | 12/1985 | Osborne |
| 4,983,381 A | 1/1991 | Zaragoza |
| 4,990,089 A | 2/1991 | Munro |
| 5,078,604 A | 1/1992 | Malmin |
| 5,104,315 A | 4/1992 | McKinley |
| 5,365,624 A | 11/1994 | Berns |
| 5,443,386 A | 8/1995 | Viskup |
| 5,487,662 A | 1/1996 | Kipke et al. |
| 5,513,986 A | 5/1996 | Feltham et al. |
| 5,575,654 A | 11/1996 | Fontenot |
| 5,682,904 A | 11/1997 | Stinnett |
| 6,077,073 A | 6/2000 | Jacon |
| 6,152,733 A | 11/2000 | Hegemann et al. |
| 6,254,391 B1 | 7/2001 | Darnell |
| 6,343,932 B1 | 2/2002 | Wiesel |
| 6,364,665 B1 | 4/2002 | Trettenero |
| 6,439,889 B1 | 8/2002 | Chen et al. |
| 6,616,447 B1 | 9/2003 | Rizoiu |
| 6,893,259 B1 | 5/2005 | Reizenson |
| 6,981,874 B2 | 1/2006 | Allred et al. |
| 7,118,377 B2 | 10/2006 | Inoue et al. |
| 7,331,784 B2 | 2/2008 | Suzuki |
| 7,775,795 B2 | 8/2010 | Khawaled et al. |
| 8,029,278 B1 | 10/2011 | Levine |
| 8,205,618 B2 | 6/2012 | Berghash et al. |
| 8,215,954 B2 | 7/2012 | Levine |
| 8,277,215 B2 | 10/2012 | McLean et al. |
| 2001/0038997 A1 | 11/2001 | Lindquist |
| 2002/0110780 A1 | 8/2002 | Zegarelli |
| 2002/0137001 A1 | 9/2002 | Cipolla et al. |
| 2003/0104341 A1 | 6/2003 | Zavitsanos et al. |
| 2005/0037315 A1 | 2/2005 | Inoue et al. |
| 2005/0196725 A1 | 9/2005 | Fu |
| 2006/0029908 A1 | 2/2006 | Allred et al. |
| 2007/0015112 A1 | 1/2007 | Hochman et al. |
| 2007/0184404 A1 | 8/2007 | Johnki |
| 2007/0259316 A1 | 11/2007 | Conrad et al. |
| 2008/0233541 A1 | 9/2008 | De Vreese et al. |
| 2009/0087812 A1 | 4/2009 | Andersen |
| 2009/0123886 A1 | 5/2009 | Vaska |
| 2011/0027746 A1 | 2/2011 | McDonough et al. |
| 2011/0076636 A1 | 3/2011 | Wolff et al. |
| 2011/0104633 A1 | 5/2011 | Levine |
| 2011/0185525 A1 | 8/2011 | Stapelbroek et al. |
| 2011/0189626 A1 | 8/2011 | Sanzari |
| 2012/0156648 A1 | 6/2012 | Kaufman et al. |
| 2017/0079746 A1* | 3/2017 | Sanders ............... A61C 19/066 |
| 2017/0252117 A1* | 9/2017 | Sanders ............... A61B 46/40 |

FOREIGN PATENT DOCUMENTS

| | | |
|---|---|---|
| WO | 2011/014619 A1 | 2/2011 |
| WO | 2013039906 A1 | 3/2013 |
| WO | 2015/186051 A2 | 12/2015 |

OTHER PUBLICATIONS

Office Action from the Eurasian Patent Office, Application No. 201490628/31 dated Feb. 12, 2016.

International Search Report and Written Opinion, PCT/US2012/054652, dated Nov. 13, 2012.

International Preliminary Report on Patentability, PCT/US2012/054652, dated Mar. 12, 2014.

Goldberg et al., "Tooth Bleaching Treatments", L' eclaircissement dentaire—evaluation des therapeutiques, 2005 Association Dentaire Francaise, Paris, pp. 1-50; www.prgmea.com/docs/tooth/20.pdf.

International Search Report, Application No. PCT/IB2015/054154 dated Nov. 27, 2015.

Written Opinion, Application No. PCT/IB2015/054154 dated Nov. 27, 2015.

* cited by examiner

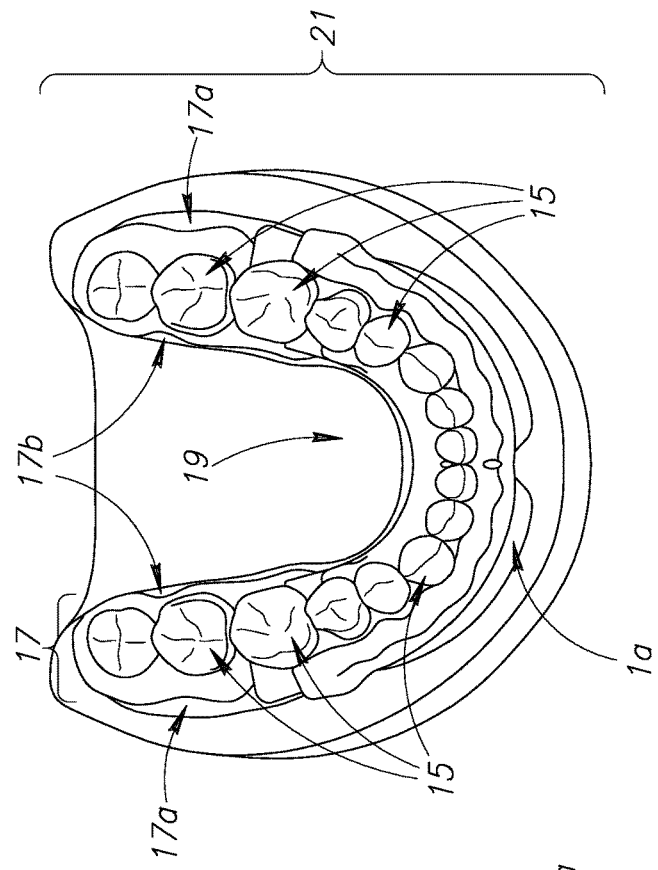
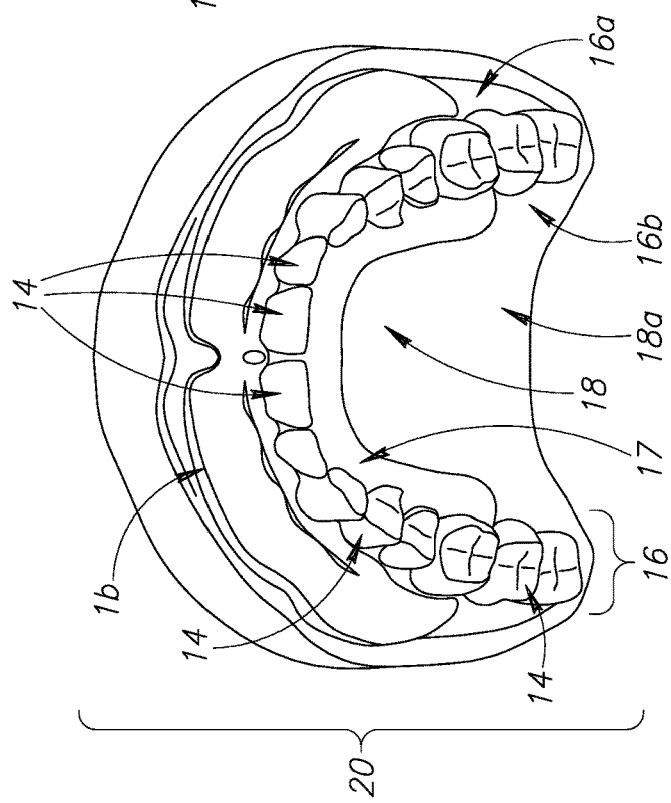
FIG.9B
FIG.9A

ANATOMICAL ADAPTABLE DRAPE DEVICE

FIELD OF THE INVENTION

The present invention relates to methods and devices useful in providing drapes or covers for anatomical parts, such as during treatment of the parts, particularly but not exclusively to oral drapes for dental treatments.

BACKGROUND OF THE INVENTION

In dental medicine, many treatment materials are typically placed within the oral cavity on the hard (teeth) tissues and soft (inner mucosal epithelium of the cheek, lips, and gingiva and the tongue) tissues.

These treatment materials are placed topically on these tissues or may be inserted (injected) in the space between them, for example, in the naturally occurring sulcus at the tooth/gum line.

These treatment materials are typically applied to the tissues in an "open" manner, namely, without any covering material or containment device. This significantly reduces their desired therapeutic effect as the materials are immediately exposed to saliva contamination (containing numerous pathogenic microorganisms) and salivary washout (or fluid/solids ingestion washout) in a very short time. This time range can be as short as a few seconds to around 10 minutes or more, depending on salivary flow, the viscosity of the treatment material or whether the patient ingests solids or liquids after application of the treatment material.

Additionally, currently known devices use a cover device that covers both the teeth and the gums. These are typically custom made to a specific patient using the following fabrication method. Dental molds are taken of the patient's teeth and surrounding gums and dental stone cast models are poured and allowed to harden. These cast models are removed from the molds and a vacuum-formed thin plastic custom made tray for that specific patient is formed and trimmed to cover over both the teeth and a narrow portion of the surrounding gums. These typically leak the treatment material out of them and also allow saliva to seep inside of them as the stiff material of the tray is difficult to adapt closely to the undulating and varied topography of the teeth and surrounding gums of each individual patient which they are meant to cover.

Additionally, patches onto whose inner surface a thin layer of treatment layer has been adhered are used to cover small areas of the gum tissue. Due to their size they can only treat very limited areas of the soft tissues of the oral cavity and cannot be used to treat the teeth as they cannot be adhered to the teeth structure. They are also easily dislodged by the tongue or contact with the inner cheek and lip muscles.

Additionally, light curable foam materials are manually applied to the gingiva to create a protective barrier against high concentration applications of peroxide for professional teeth whitening treatments. The application of these materials are manually intensive and require a high skill level to apply. Additionally, they are often highly brittle and tend to break or fall off the gingiva and are easily dislodged when even slight pressure or flexing force is applied to them. They are therefore unsuitable to use a gingival barrier in conjunction with an intra-oral mouthpiece.

Additionally, rubber dam barriers consisting typically of some form of latex or rubber sheet or barrier are applied to provide for a "dry field" so as to prevent saliva ingress or moisture contamination during many dental procedures. The rubber dams are typically made of latex rubbers and require manually punched holes by the dentist to allow for them to be placed through the anatomical crown portions of the teeth so as to allow them to drape over the surrounding gum tissue and other oral structures of the oral cavity. These rubber dam barriers are typically fixed or retained in the mouth by using some type of clamping apparatus to secure or anchor the dam barrier in the mouth. These devices are typically very cumbersome and very large, uncomfortable for the patient and due to their size and coverage of large areas of the intra-oral anatomical structures, preclude their use in conjunction with the insertion of an intra-oral mouthpiece in the mouth.

It is an object of the present invention to provide an improved device that aims to overcome or at least alleviate the above mentioned drawbacks.

SUMMARY OF THE INVENTION

In accordance with a first aspect of the present invention, there is provided an anatomical drape for covering a treatment area of an anatomical part, the drape comprising an elastomeric material capable of conforming to the contours of the anatomical part and including a curing agent wherein activation of the curing agent causes hardening of the material to set the drape in a configuration conforming to the anatomical part.

In some embodiments an anatomical drape is provided for covering a treatment area of an anatomical part, the drape comprising: an elastomeric material capable of conforming to the contours of the anatomical part; and one or more internal channels containing uncured curing material;
   wherein the uncured curing material is adapted to be cured, thereby becoming hardened to at least partially set the drape in a configuration conforming to the anatomical part.

In some embodiments an anatomical drape in provided, wherein the elastomeric material of the drape is substantially liquid impermeable and gas permeable, both before and after curing.

In some embodiments an anatomical drape is provided, wherein the drape is configured to generally conform to an oral anatomy.

In some embodiments an anatomical drape is provided, wherein the drape conforms to a gum ridge anatomy, wherein the drape forms an enclosed protective cover over the gum ridge with optional holes for passage of erupted teeth there through.

In some embodiments an anatomical drape is provided, wherein the drape conforms to a portion of the gum ridge anatomy, wherein the drape forms an enclosed protective cover over the gum ridge with optional holes for passage of erupted teeth there through.

In some embodiments an anatomical drape is provided, wherein the drape conforms to the gum ridge anatomy, wherein the drape forms an enclosed protective cover over the gum ridge with optional holes for passage of erupted teeth there through and substantially full coverage over portion of the gum ridge that are edentulous.

In some embodiments an anatomical drape is provided, wherein a curing material is distributed inside the internal channels to conform the drape to the anatomical structure covered by the drape.

In some embodiments an anatomical drape is provided, further comprising an external energy source usable to activate the curing material.

In some embodiments an anatomical drape is provided, wherein the energy source is one or more sources selected from the set including heat and/or light.

In some embodiments an anatomical drape is provided, wherein the curing material is a light curable agent selected from the group consisting of blended mixtures of oligomers, fillers and photo-initiators.

In some embodiments an anatomical drape is provided, wherein one or more treatment material layers are included on at least one surface of the drape.

In some embodiments a kits of parts for covering a treatment area is provided, the kit comprising one or more drapes as described herein and a light source In some embodiments the kit further comprises one or more therapeutic sources.

In some embodiments the kit further comprises one or more treatment sources.

In some embodiments a method for the manufacture of an anatomical drape for covering a treatment area of an anatomical part is provided, the method comprising the steps of: (a) configuring a drape device by preparing a set of inserts that mirror the shape of internal channels and septum plugs of the drape device; (b) molding elastomeric materials onto the set of inserts in order to produce a set of elastomeric spacers; (c) inserting the set of inserts with spacers into a second mold and clamping them in place in the second mold; (d) over-molding with similar elastomeric materials to create outer aspects of the elastomeric drape, (e) removing the set of inserts where the spacers remain to prepare a set of internal channels and self-sealing septum plugs inside the body of the drape; and (f) inserting one or more flowable uncured curing material(s) through the set of self-sealing septum plugs into the internal channels of the drape so as to at least partially fill the internal channels with uncured curing materials.

In some embodiments the method further comprises applying a second or additive into the internal channels.

In some embodiments an oral drape for covering a treatment area of an oral cavity is provided, the drape comprising an elastomeric material capable of conforming to the contours of the oral anatomical part and including a curing agent contained within internal channels distributed with in the drape wherein activation of the curing agent causes hardening of the material to at least partially set the drape in a configuration conforming to the anatomical part, the set drape being substantially gas permeable but liquid impermeable.

In some embodiments the drape is adapted to be applied and conformed to a gum ridge and to a mouthpiece that substantially covers the teeth and gum ridge or ridges, to provide for a continuous fluid seal of the mouthpiece treatment cavities to the drape(s).

DESCRIPTION OF THE DRAWINGS

The principles and operation of the system, apparatus, and method according to the present invention may be better understood with reference to the drawings, and the following description, it being understood that these drawings are given for illustrative purposes only and are not meant to be limiting, wherein:

FIG. 2 is a transparent top and side view according to some embodiments of a lower (mandibular) oral drape 1a;

FIG. 4 is a transparent bottom view according to some embodiments of a lower oral drape 1a;

FIG. 5 is a bottom view according to some embodiments of a lower oral drape 1a;

FIGS. 6A and 6B are transparent top and side views according to some other embodiments of a lower oral drape 1a;

FIG. 7 is a transparent top and side view according to some other embodiments of a lower oral drape 1a;

FIG. 9a is a top and front view of a model of the maxillary jaw oral structures 20;

FIG. 9b is a top view of a model of the mandibular jaw oral structures 21, and the lower oral drape 1a applied onto the mandibular gum ridge 17; and FIG. 10 is a side view of some embodiments of an upper oral drape 1b and lower oral drape 1a.

DETAILED DESCRIPTION OF THE INVENTION

Figure 1:
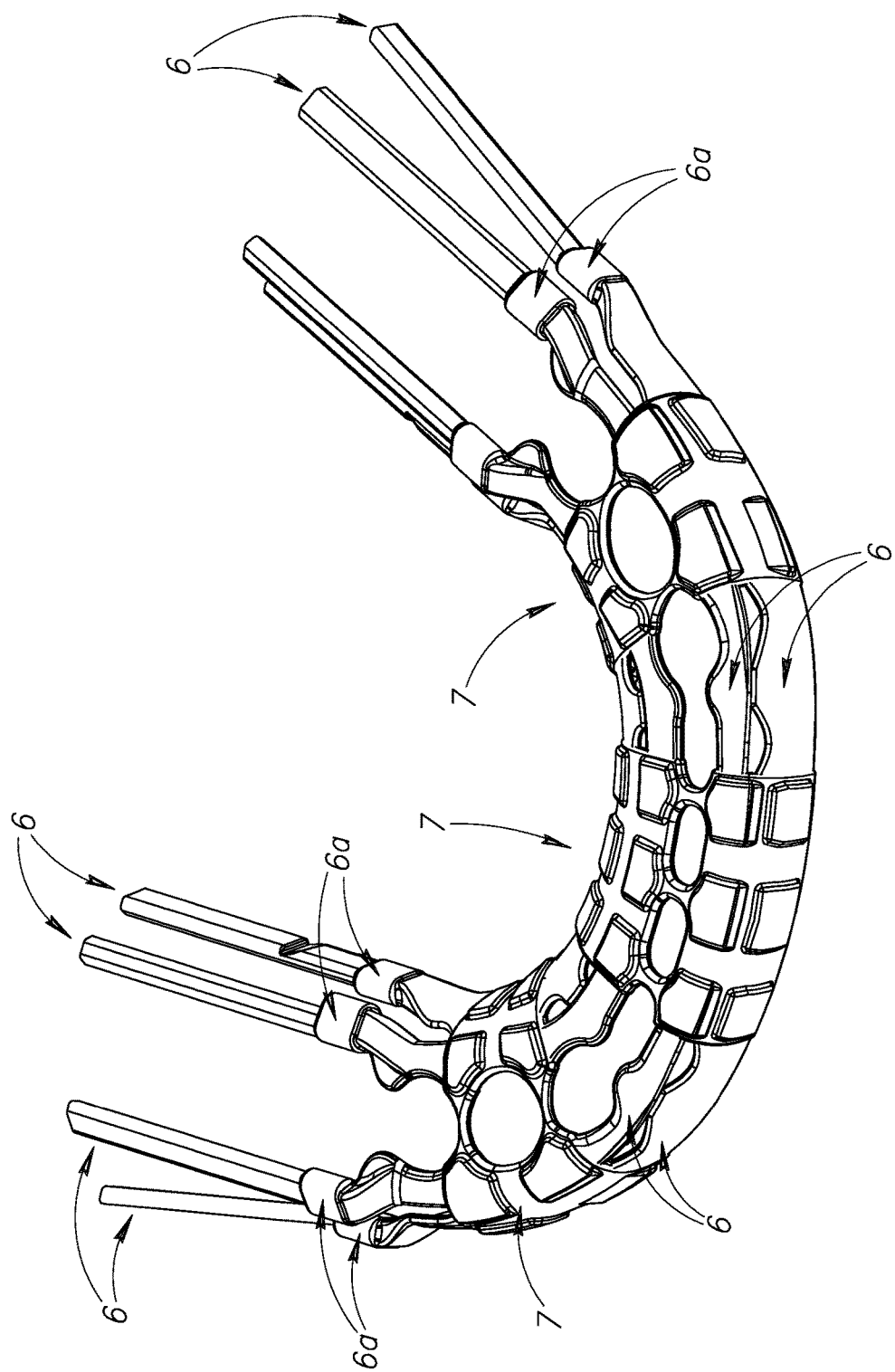
FIG. 1 is a top and side view of gum drape inserts 6 with molded insert spacers 7, according to some embodiments.

The following description is presented to enable one of ordinary skill in the art to make and use the invention as provided in the context of a particular application and its requirements. Various modifications to the described embodiments will be apparent to those with skill in the art, and the general principles defined herein may be applied to other embodiments. Therefore, the present invention is not intended to be limited to the particular embodiments shown and described, but is to be accorded the widest scope consistent with the principles and novel features herein disclosed. In other instances, well-known methods, procedures, and components have not been described in detail so as not to obscure the present invention.

The word "drape" as used herein may encompass various protective materials with or without adhesives that may be utilized to cover, dress or place over a target area or object(s) while undergoing a treatment, to cover or protect a target area, and optionally prevent the flow of liquids or materials from or to the target area.

In accordance with a first aspect of the present invention, there is provided an anatomical drape for covering a treatment area of an anatomical part, the drape comprising an elastomeric material capable of conforming to the contours of the anatomical part and including a curing agent wherein activation of the curing agent causes hardening of the material to set the drape in a configuration conforming to the anatomical part. The anatomical part preferably comprises an oral anatomy. However, it is to be appreciated that a drape may be provided to cover any anatomical part, such as a limb (or portion of a limb).

More preferably, the drape conforms to a gum ridge anatomy with the drape forming an enclosed protective cover over the gum ridge or part of the gum ridge. The drape may comprise a partial or full U-shaped arch which is then tailored to the actual oral anatomy to provide a high level of conformity. The drape, in some embodiments, may be provided with pre-perforated holes for easy removal and passage of the anatomical crown portions of the teeth there-through or pre-configured cut-out holes may be provided of varying shapes and dimensions for receipt of anatomical crown portions of the erupted teeth there-through whereby the anatomical crown portions of the teeth remain substantially uncovered and exposed to the oral cavity whilst the surrounding gum tissue and gum ridge are substantially covered by the drape. Some portions of the gum ridge may be edentulous and the gum drape in these segments may not have cut out holes so as to substantially cover these segments of the gum ridge. This embodiment of the oral drape may be advantageous to apply over newly placed dental implant sites.

The preformed shape of the drape is formed to generally conform to the shape of a portion of the oral cavity or other body part to facilitate easy and rapid insertion and removal of the drape from the target area.

The preformed drape may cover only the gum ridge or a portion of the gum ridge whilst in the main or entirely not covering the hard or soft palate, mucco-buccal folds, tongue, inner surfaces of the cheek or lips, and the floor of the mouth or airway.

The curing agent/material may be distributed inside the drape in internal channels of various configurations within the body of the drape. When the curing agent is polymerized, this will provide a semi-rigid drape that conforms to a particular individual anatomy while allowing its removal and enhancing comfort to the user.

Preferably, the elastomeric material of the drape is substantially liquid impermeable and gas permeable, both before and after curing. In some embodiments, the elastomeric material has high tear strength properties.

More preferably, the drape is comprised of an elastomeric material with a relatively low modulus of Young, relatively high elongation, relatively high tear strength and relatively low recoil properties. Any suitable curing agent/material may be used but preferably the curing agent/material is a flowable material suitable for insertion into the empty internal channels of the drape and may be activated (cured/polymerized) by an external source, such as heat and/or light source or combination thereof.

Preferably the mechanical properties of the drape resist tearing when placing the tooth holes over and through the anatomical crowns of the teeth and allowing for the interdental bridges of the drape between the teeth to be snapped through the interproximal (interdental) teeth contact areas between the teeth without tearing the bridges while allowing the bridges to seat firmly down between the teeth (interproximally/interdentally) at the level of the gum line.

Preferably the mechanical properties of the drape interdental bridges allow them to be stretched so as to thin them and allow for easy insertion of the interdental bridges through the contact areas between the teeth.

The seating of the intact interdental bridge portions below the contact areas is vital for achieving a snug circumferential fit of the drape around the cervical necks of the anatomical crown portions of the erupted teeth and a good seal of the surrounding gum tissue at the level of the gum line with the drape of the present invention.

The drape's internal channels may preferably be filled in with uncured curing agent/material at their manufacturing site and packaged in light impermeable sleeves or bags. The curing agent/material in its uncured form should ideally allow for a sufficient working time for the operator to apply the drape properly in the mouth once the drape is removed from its protective packaging. The curing material or agent upon hardening should preferably be capable of constraining the stretched buccal and lingual aspects of the drape to the gum lines of the teeth while providing for a drape that still remains flexible to a degree that provides patient comfort and ease of removal after use.

The drape containing the uncured curing agent/material may be individually stretched by the operator to the level of the gum line of each individual tooth on either its buccal or lingual/palatal aspects or stretch and constrained for a group of teeth in the following manner. Applying a curing light to polymerize the curing agent/material will harden this segment of the internal channel(s) of the drape and constrain the recoil properties of this segment of the drape material from returning to their un-stretched shape. This procedure may be repeated independently on both either or both of the buccal and lingual aspects of the tooth or teeth so as to sequentially conform the drape structure and adapt it to the specific gum lines of any patient both for the upper and or lower full dental gum ridges or portions of the upper and or lower gum ridges.

Other internal channels may be incorporated in the drape and filled with uncured curing agent/material. When cured, these will allow the operator to intimately conform the drape to the specific gum ridge anatomy of any patient and so allow for a very snug fit of the drape to the patient's specific gum ridge anatomy so as to provide for a superior seal of the drape on the gum ridge from any external caustic agents such as high concentration peroxide whitening agents or alternatively, to effectively contain and prevent the leakage or saliva washout of medicaments or therapeutic agents applied underneath the drape prior to placement of the drape.

Preferably the uncured curing agent/material allows for a sufficient working time for the operator (dentist or hygienist) to place the drape over and through the anatomical crowns of the teeth, and closely adapt the drape the specific gum lines and gum ridge anatomy of any patient before hardening the curing agents contained within the internal channels of the drape.

The now snugly fitted drape can now also be utilized as an effective wound dressing or containment barrier for medicaments or therapeutic agents applied to, for example, the periodontal pockets of the gums surrounding the teeth and or the gum ridges prior to insertion and adaptive conformation of the drape as previously described.

This allows for these medicaments or therapeutic agents to be maintained in high concentrations on or in the drape covered target soft tissues by effectively preventing them from leaking out and preventing the saliva from diluting and washing them out as well. Maintaining these medicaments or therapeutic agents in place at high concentrations on or in the target tissues significantly extends their exposure time and therefore their therapeutic window of action. This ability of the drape of the present invention may allow for achieving significantly enhanced therapeutic outcomes with these medicaments or therapeutic agents particularly for patients with impaired healing such as diabetics who suffer from chronic periodontitis.

Medicaments or therapeutic agents may also be pre-applied or pre-impregnated into the inner surfaces of the drape at the time of manufacture for time released application to the gingival tissues of the gum ridges or for timed delivery into the periodontal sulcus of the teeth.

Suitable drape elastomeric materials include, but are not limited to TPE's (thermoplastic elastomers; TPU's (thermoplastic urethanes); elastomeric silicones (RTV, HTV, LSR), the material preferably being both substantially liquid impermeable and gas permeable (i.e., breathable). Preferably, the material contains millions of micro-pores per square cm.

The drape may include one or more treatment material layers on at least one surface of the drape, for example for neutralizing treatment materials. The materials are preferably provided on the inner surfaces of the drape but may also be provided on the outer surfaces of the drape.

According to additional embodiments, a septum type port or ports may be provided for accessing the internal channels of the drape for receiving a tool, such as a syringe needle(s) for the delivery of the uncured curing agent/materials into the channels.

These septum type ports or plugs may be made of the same material as the drape itself and may also be self-sealing so as to self-seal upon removal of the syringe needle after delivering the uncured curing agent into the internal channels of the drape.

A second aspect of the present invention provides a kit of parts for installing an anatomical drape, the kit comprising a drape according to the first aspect of the present invention and a light source, optionally with at least one further drape and/or a therapeutic or other treatment source.

A third aspect of the present invention provides a method for the manufacture of an anatomical drape, preferably being a drape according to the first aspect of the present invention, the method comprising the steps of: (a) preparing a set of inserts that mirror the shape of the internal channels and septum plugs of the drape device; (b) molding elastomeric materials onto the set of inserts in order to produce a set of elastomeric spacers (c) inserting the set of inserts with spacers into a second mold and clamping them in place in the second mold; (d) over-molding with the same or similar elastomeric materials to create the "body" outer inner aspects of the elastomeric drape, (e) removing the set of inserts where the spacers remain and have now fused with body material of the drape and where upon removal of the inserts a set of internal channels and septum plugs now remain inside the body of the drape; (f) inserting flowable uncured curing agent/material(s) through the set of septum plugs into the internal channels of the drape so as to fill the channels with uncured curing agent/materials.

Step (f) the septum plugs may be self-sealing and so prevent leakage out, of the applied uncured curing agents. The step of introducing the uncured curing agent/materials and packaging the final product should preferably be accomplished under "red light" manufacturing conditions to prevent the premature curing of the curing agent/material(s).

FIG. 1 is a top side view according to some embodiments; wherein are depicted a set of gum drape inserts 6 incorporating insert septum plug segments 6a, onto which have been molded elastomeric gum drape spacers 7. A drape may be constructed with a plurality (preferably two or more, more preferably three or more) of the gum drape spacers 7. For example, the drape may include three gum drape spacers 7 as shown in FIG. 1.

Figure 2:
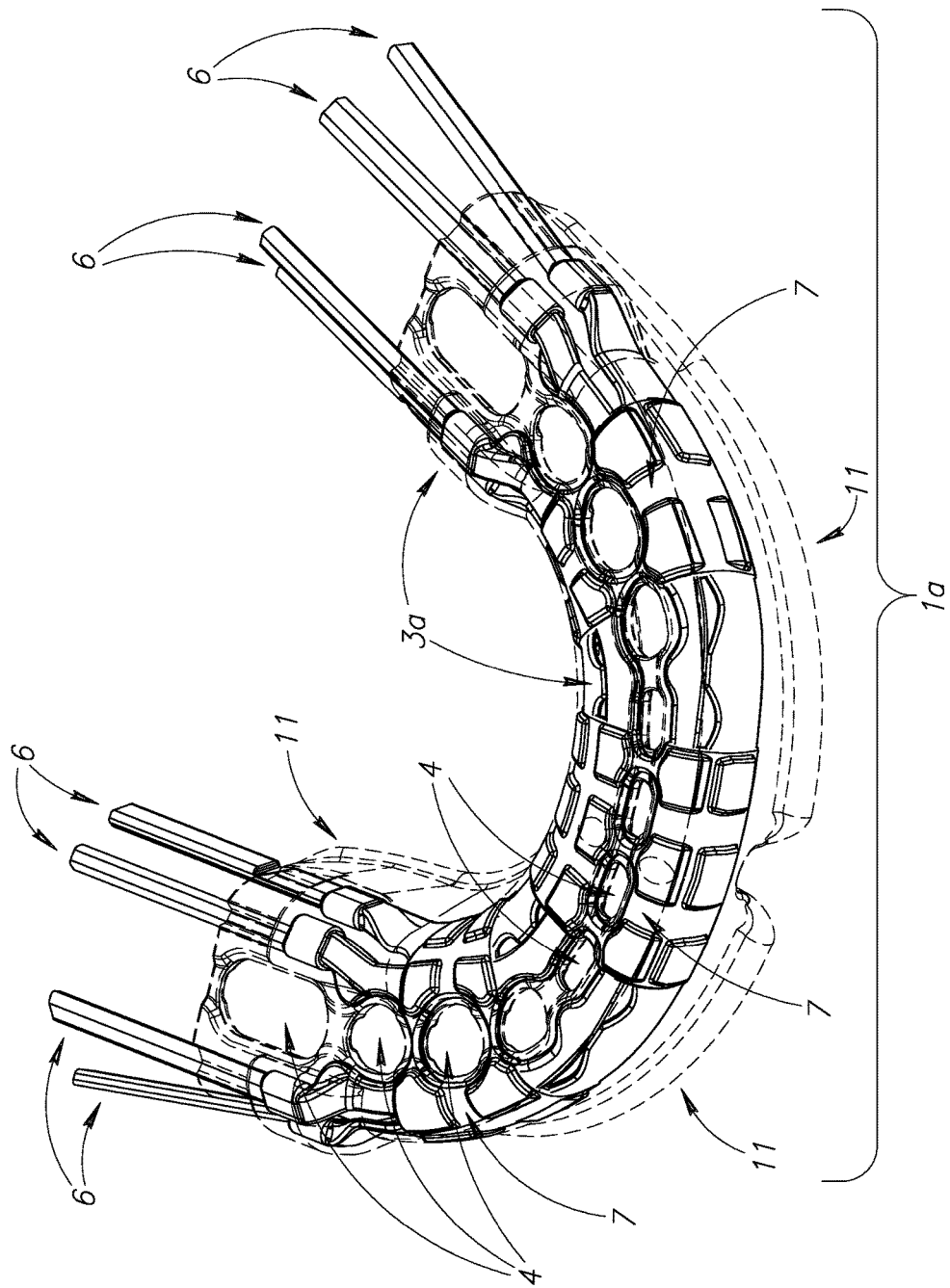

FIG. 2 is a transparent top and side view according to some embodiments of a lower oral drape 1a; wherein are depicted a set of gum drape inserts 6 before removal from between the upper layer 3a and lower layer 3b of the lower drape 1a. Also depicted is an embodiment of the gum drape roll borders 11, the teeth holes 4, and the gum drape spacers 7 inside the upper layer 3a and lower layer 3b of the lower (mandibular) oral gum drape 1a.

Figure 3:
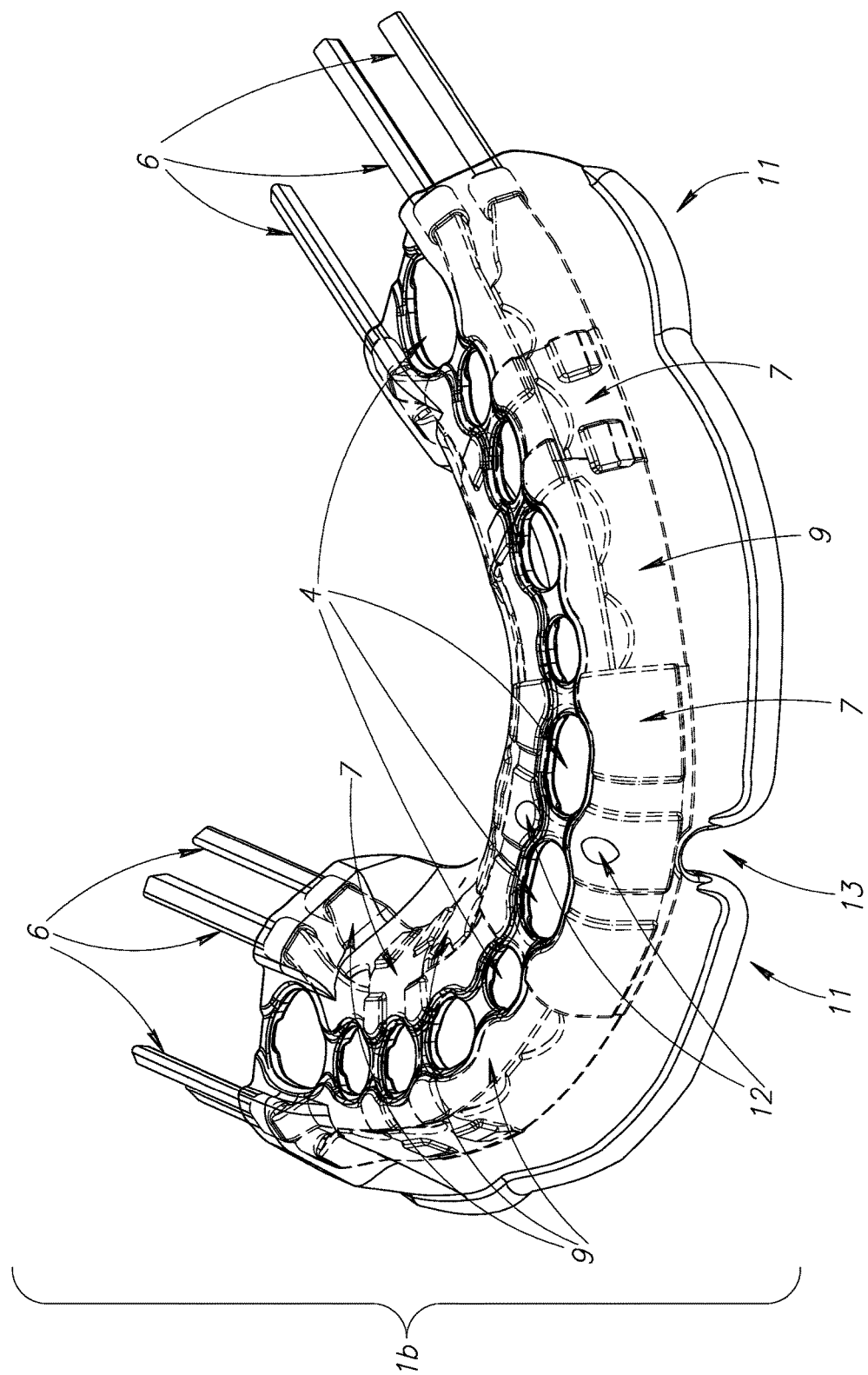
FIG. 3 is a transparent top and side view according to some embodiments of an upper (maxillary) oral drape 1b.

FIG. 3 is a transparent top and side view according to some embodiments of an upper (maxillary) oral drape 1b; wherein are depicted a set of gum drape inserts 6 before removal from between the upper layer 3a and lower layer 3b of the upper drape 1b; which upon removal, creates the built in internal channels 9 between the upper layer 3a and lower layer 3b of the upper drape 1b. Also depicted is an embodiment of the gum drape roll borders 11, the teeth holes 4, and the gum drape spacers 7 inside the upper layer 3a and lower layer 3b of the upper oral gum drape 1b as well as embodiments of gum drape positioning bumps 12 and gum drape frenulum cut out 13.

Figure 4:
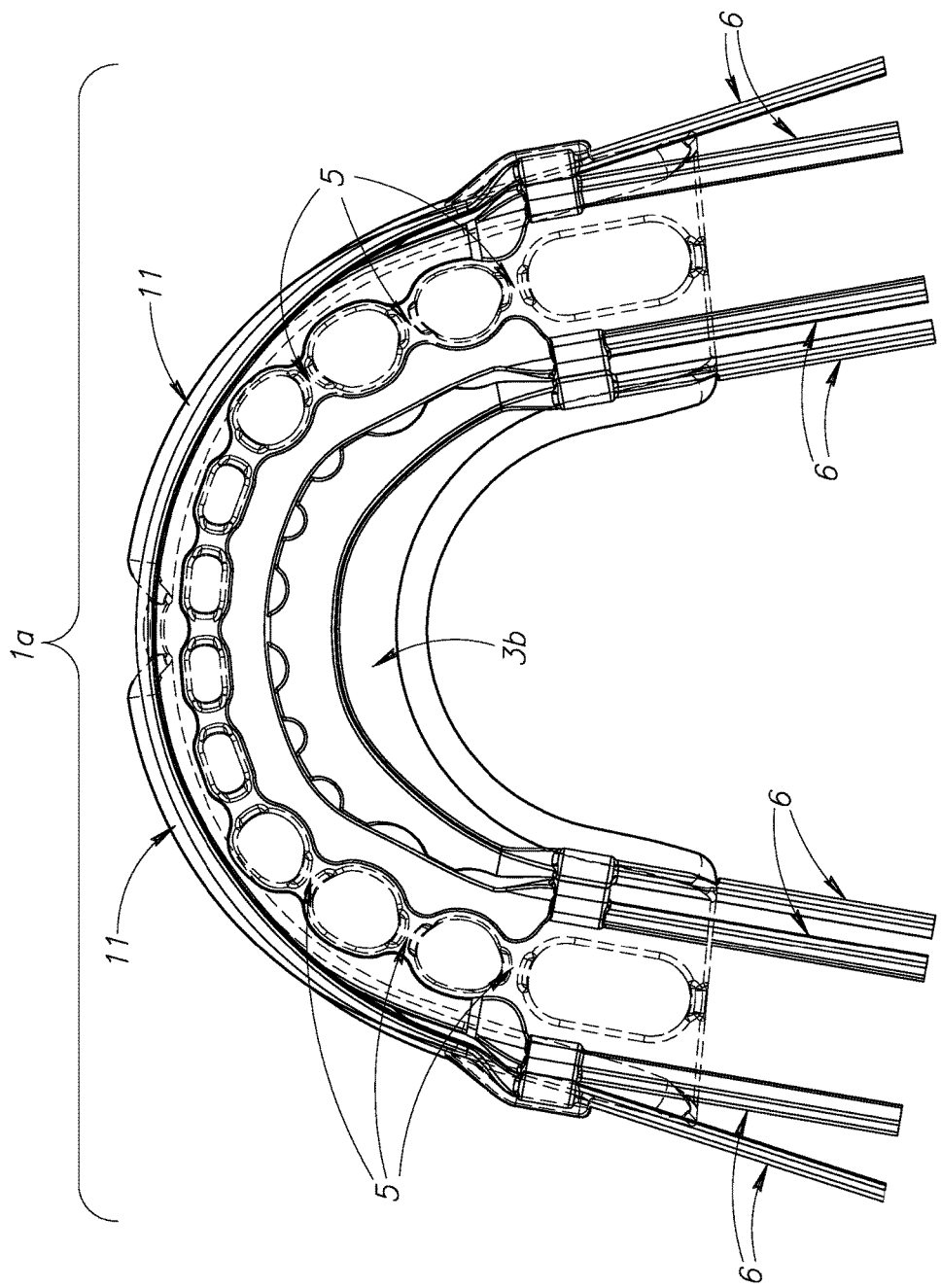

FIG. 4 is a transparent bottom view according to some embodiments of a lower oral drape 1a; wherein are depicted the lower drape surface 3b, the gum drape interdental bridges 5, a set of gum drape inserts 6 before removal from between the upper layer 3a and lower layer 3b of the lower oral drape 1a. Also depicted are embodiments of the teeth holes 4 and the buccal segments 4a and lingual segments 4b of the teeth holes 4 as well as the border roll 11.

Figure 5:
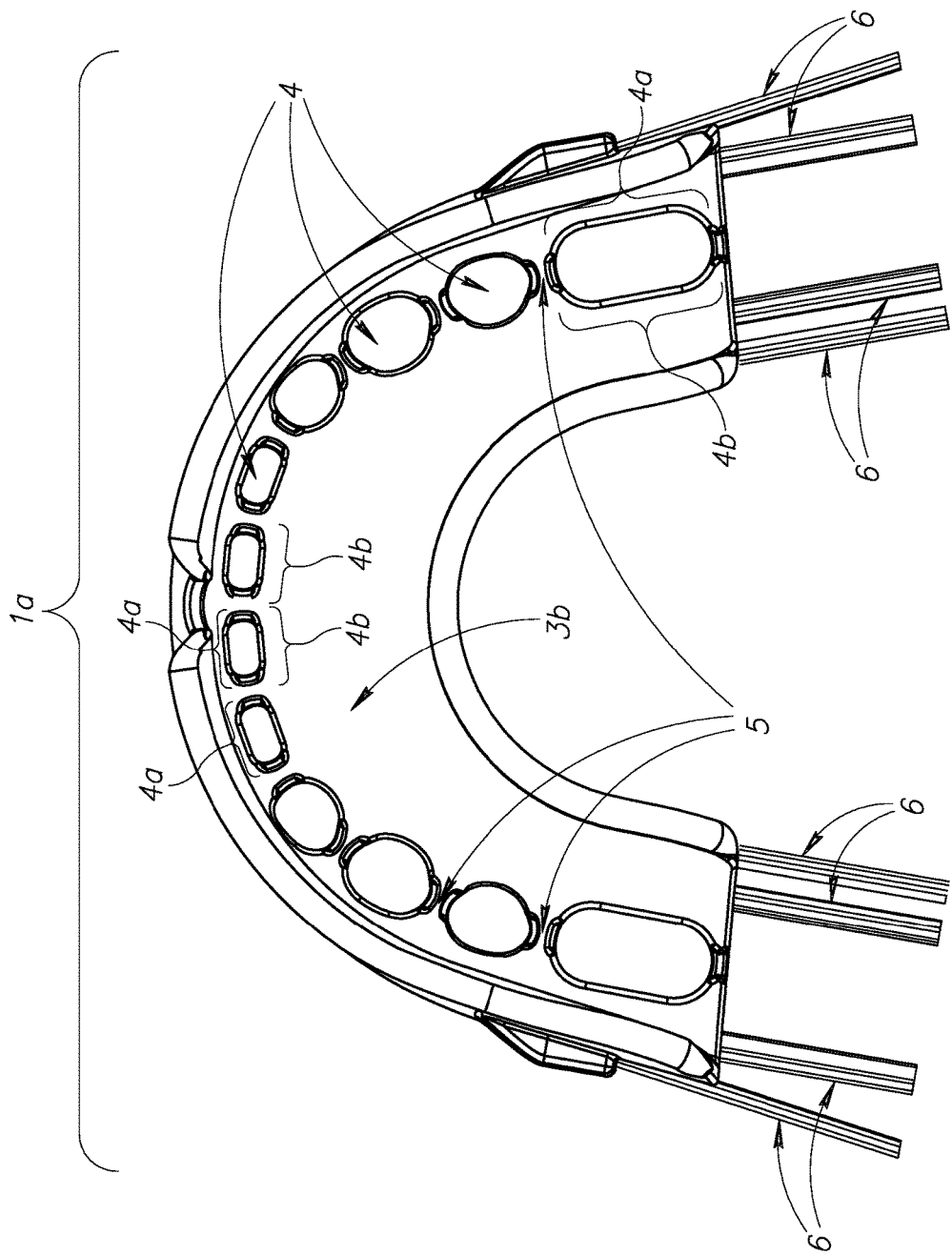

FIG. 5 is a solid bottom view according to some embodiments of a lower oral drape 1a; wherein are depicted the lower drape surface 3b, the gum drape interdental bridges 5, a set of gum drape inserts 6 before removal from between the upper layer 3a and lower layer 3b of the lower oral drape 1a. Also depicted are embodiments of the teeth holes 4 and the buccal segments 4a and lingual segments 4b of the teeth holes 4.

Figure 6A:
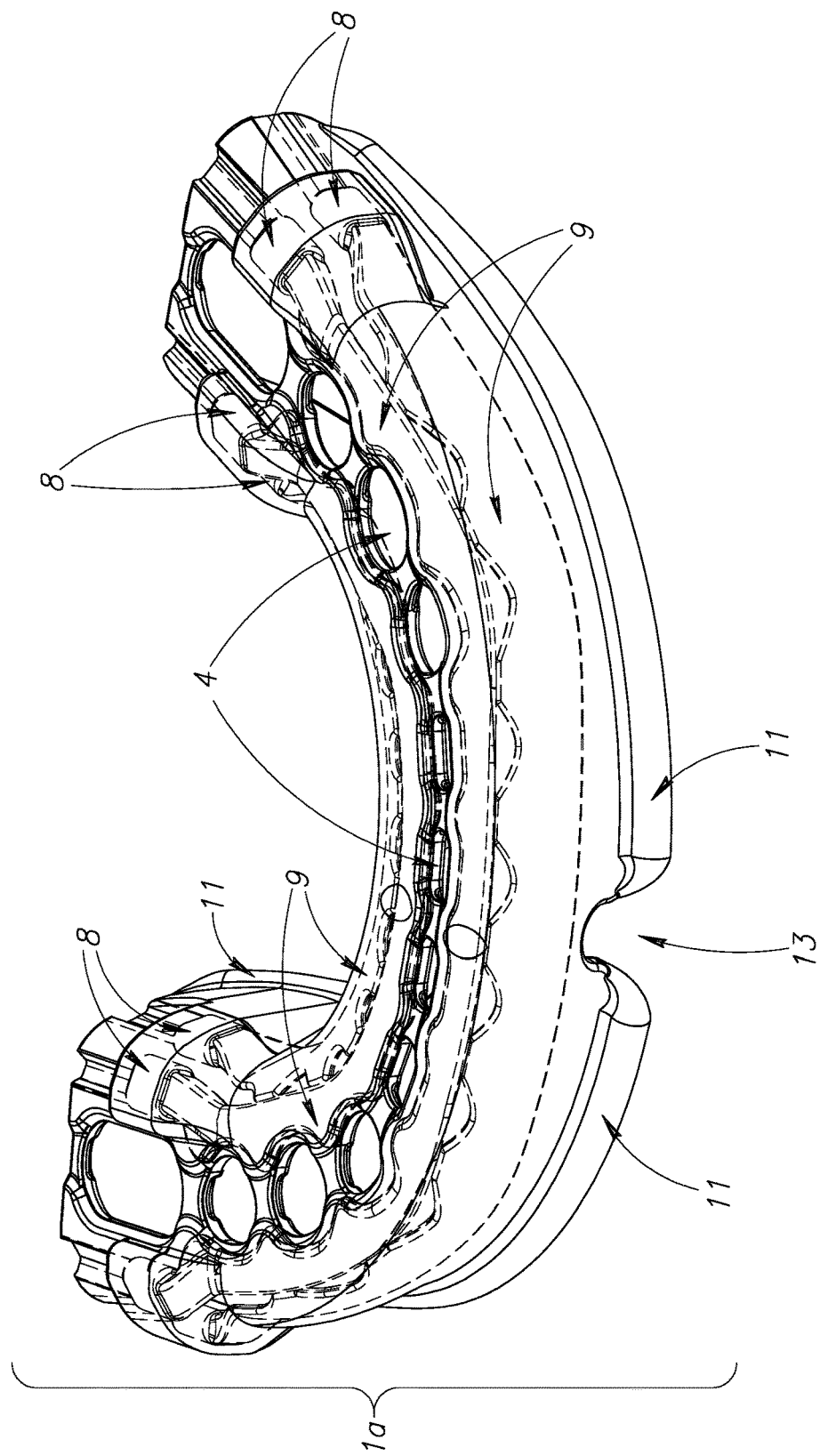

FIG. 6A is a transparent top and side view according to some other embodiments of a lower oral drape 1a; wherein are depicted septum plugs 8, a series of built in internal channels 9 between the upper 3a and lower 3b layers of the gum drape 1a, the roll border 11, and the frenulum cut out 13, and multiple teeth holes 4.

Figure 6B:
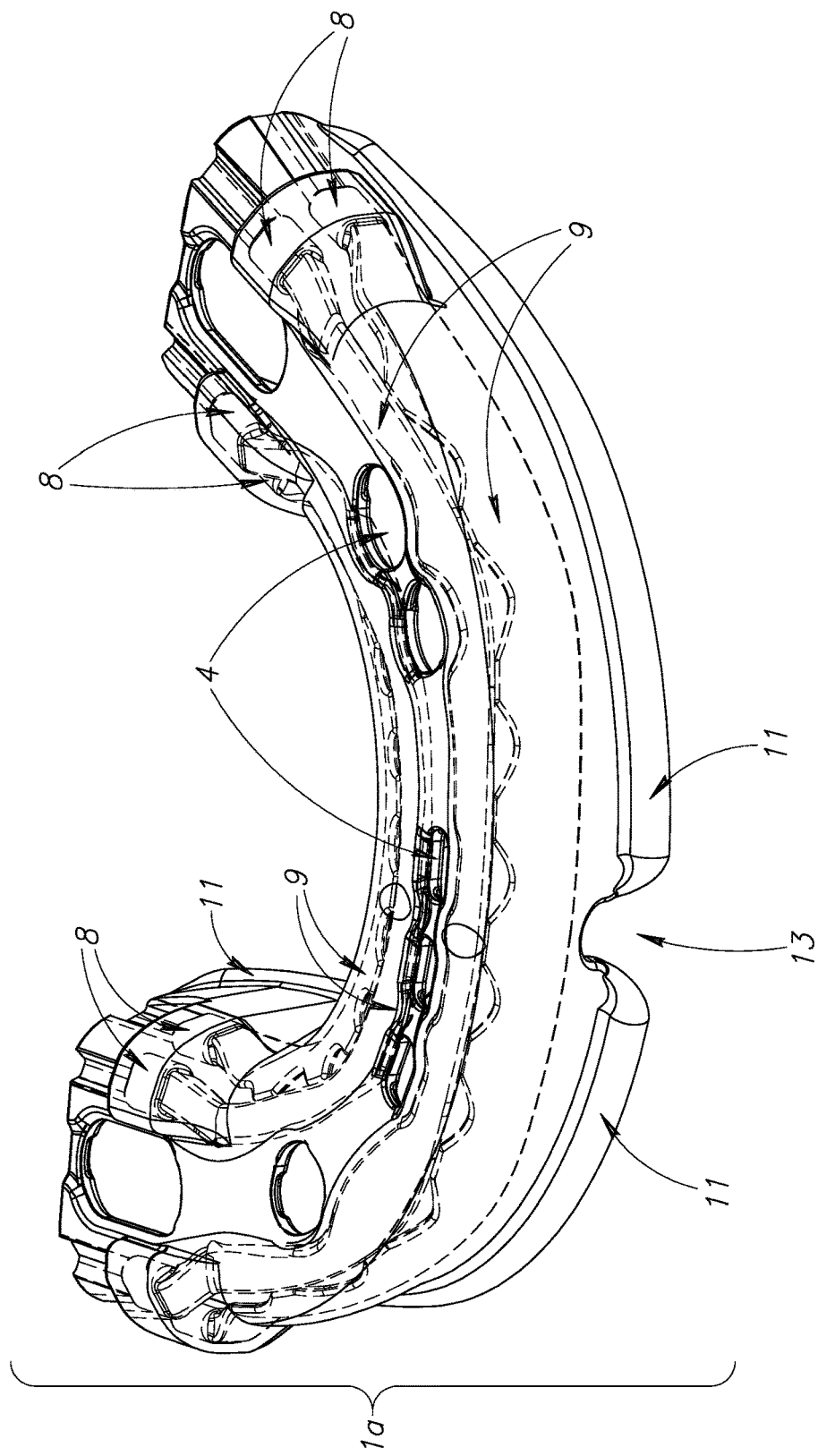

FIG. 6B is a transparent top and side view according to some other embodiments of a lower oral drape 1a; wherein are depicted septum plugs 8, a series of built in internal channels 9 between the upper 3a and lower 3b layers of the gum drape 1a, the roll border 11, and the frenulum cut out 13, with several teeth holes 4, wherein some teeth holes as per FIG. 4A are missing.

Figure 7:
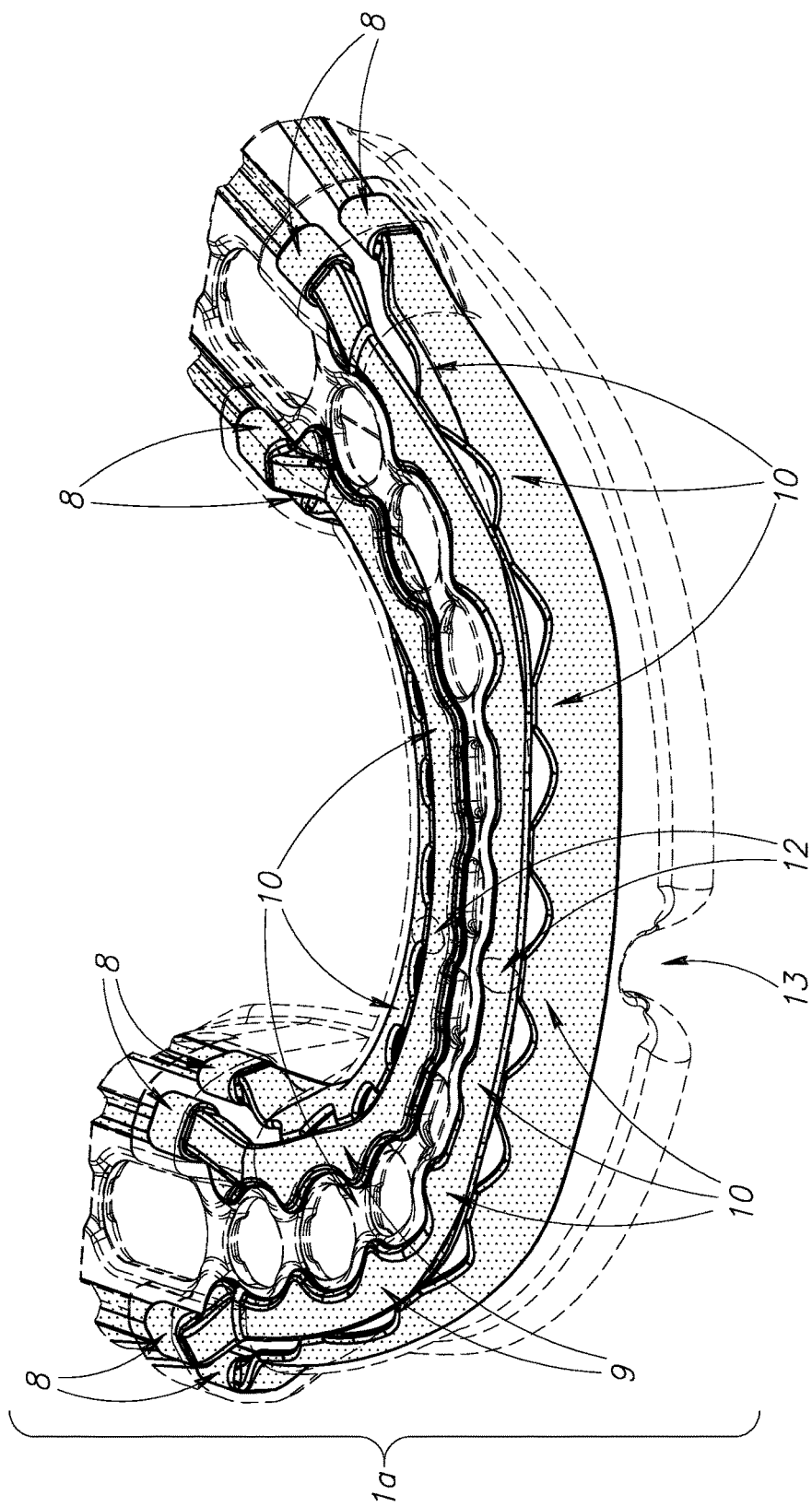

FIG. 7 is a transparent top and side view according to some other embodiments of a lower oral drape 1a; wherein are depicted the curing agents/materials 10 inside the built in internal channels 9 having been filled into the internal channels 9 through the septum plugs 8. Also depicted is one embodiment of positioning bumps 12 and the frenulum cut out 13.

Figure 8B:
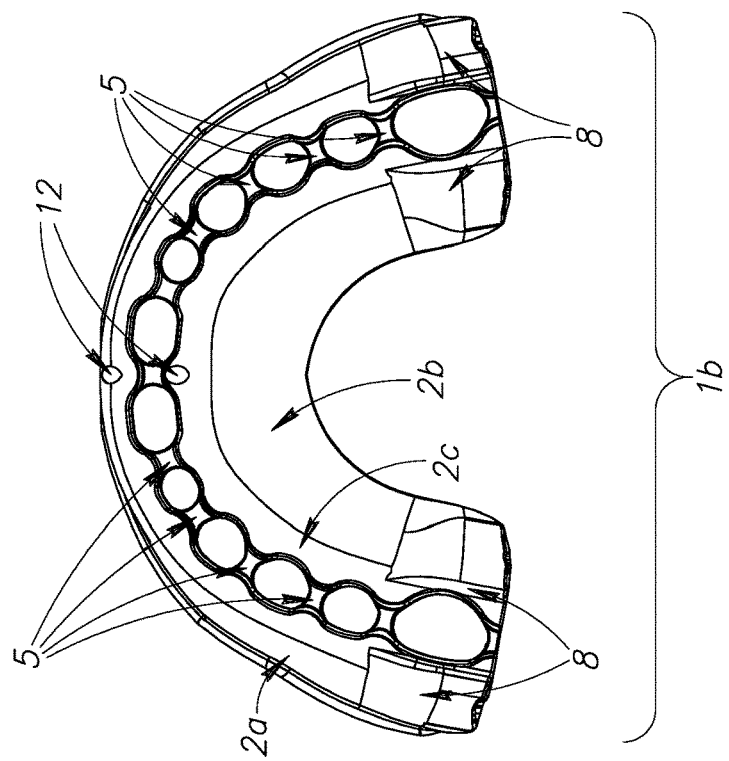
FIG. 8b is a top view according to some other embodiments of an upper oral drape 1b.
Figure 8A:
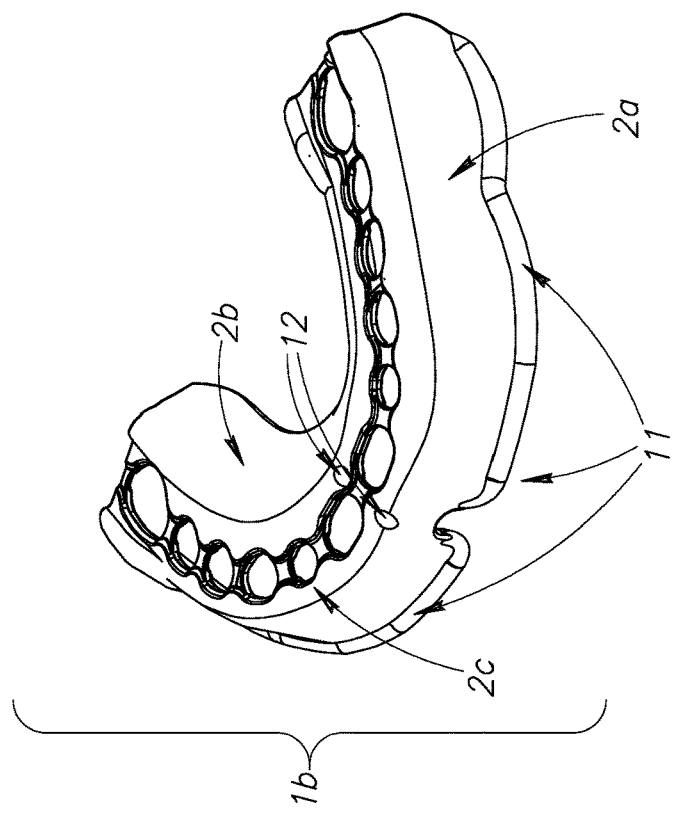
FIG. 8a is a top and side view according to some other embodiments of an upper oral drape 1b.

FIG. 8a is a top and side view according to some other embodiments of an upper oral drape 1b; wherein are depicted the buccal aspect 2a, the lingual aspect 2b, and the occlusal aspect 2c of the gum drape 1b where it is obvious that the gum drape 1a also has a buccal aspect 2a, a lingual aspect 2b, and an occlusal aspect 2c (not depicted). Also depicted is the roll border 11 of the oral drape 1b.

FIG. 8b is a top view according to some other embodiments of an upper oral drape 1b; wherein are depicted interdental bridges 5 on the occlusal aspect 2c of the oral drape 1b, the positioning bumps 12, and the buccal aspect 2a and lingual aspect 2b of the oral drape 1b.

FIG. 9a is a top and front view of a model of the maxillary jaw oral structures 20; wherein are depicted the upper oral drape 1b applied over and through the erupted anatomical crown portions of the maxillary teeth 14 and covering the maxillary alveolar gum ridge 16 on both its buccal ridge aspect 16a and its palatal ridge aspect 16b whilst in some embodiments not covering the hard 18 or soft palate 18a.

FIG. 9b is a top view of a model of the mandibular jaw oral structures 21; wherein are depicted lower oral drape 1a applied over and through the erupted anatomical crown portions of the mandibular teeth 15 and covering the mandibular alveolar gum ridge 17 on both its buccal ridge aspect 17a and its lingual ridge aspect 17b whilst in some embodiments not covering the floor of the mouth 19 or tongue (not depicted).

Figure 10:
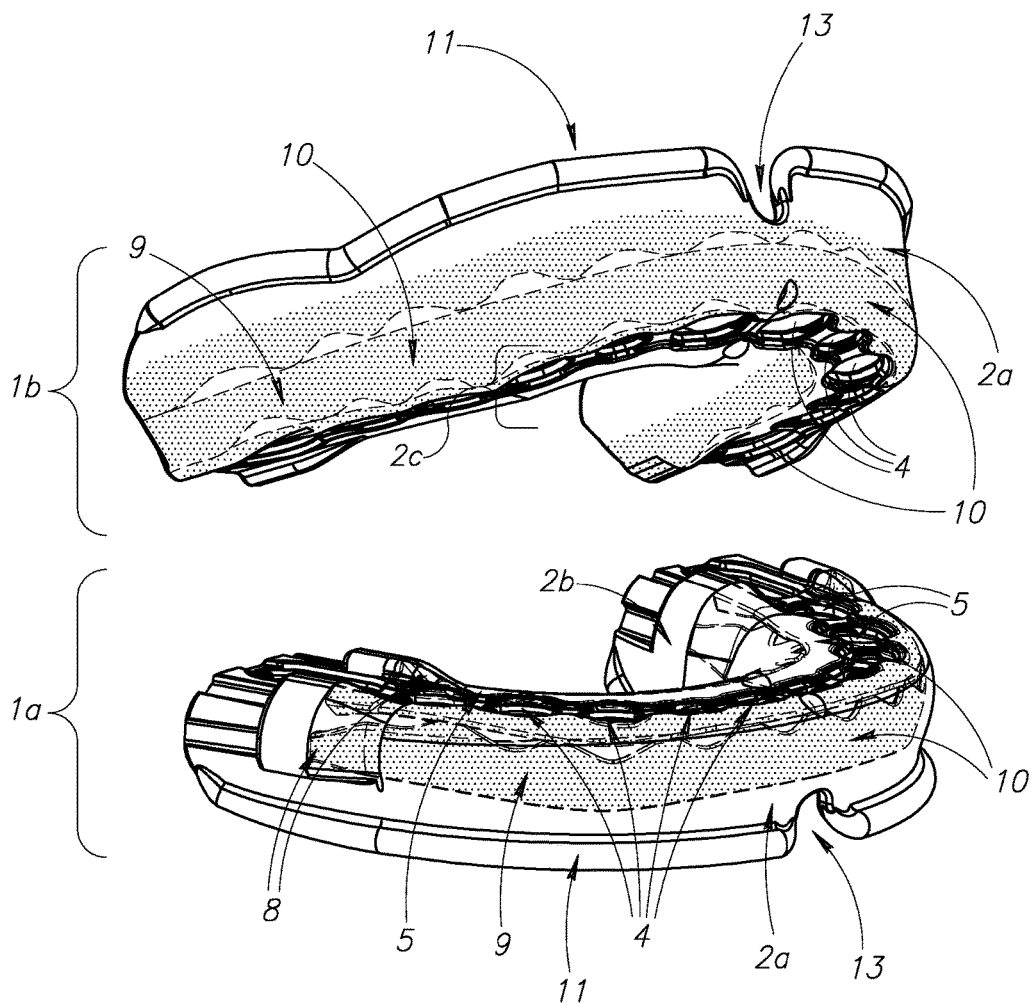

FIG. 10 is a side view of some embodiments of an upper oral drape 1*b* and lower oral drape 1*a*; wherein are depicted the teeth holes 4 and interdental bridges 5 located on the occlusal ridge aspects 2*c*, the septum plugs 8, the internal channels 9 filled with curing agents/materials 10 located on both the buccal ridge aspects 2*a* and lingual ridge aspects 2*b*. Also depicted are the roll borders 11 and frenulum notches 13.

According to some embodiments, a dental oral drape is provided, that is flexible to apply and to remove, that is designed to conform substantially to an anatomic area, and that is both liquid impermeable and gas permeable. In one example, the dental oral drape is designed to conform to the gum ridge anatomy or a portion of the gum ridge, and has pre-configured or perforated cut-out holes of various shapes and diameters for insertion over and through anatomical crown portions of the teeth (if the teeth are present), and for adaptation around or near to the gum line of the teeth, for example, as described in PCT application number WO 2013/039906 A1, by the same inventor. Of course, drapes as described herein may be used to cover and/or contain treatment areas besides the oral area, for example, in or on other bodily limbs or parts.

In some embodiments, the device includes a dental oral drape component for protection against treatment materials (such as a whitening agent) applied to the teeth that may be exposed as well to the surrounding gum tissue of the teeth that are covered (contained) by an oral tooth and/or gum treatment device being used for a treatment cavity or cavities of a mouthpiece, for example, as described in PCT patent application number WO 2013/039906 A1, by the same inventor.

In some embodiments, the dental oral drape includes a treatment material layer on one or more surfaces, wherein the treatment material is suitable for neutralizing treatment materials.

In some embodiments, the device includes a dental oral drape component which includes a gum treatment layer on its inner surfaces for the delivery of one or more therapeutic treatment materials or medicinal materials to the gums.

In some embodiments the oral drape is formed from a variety of elastomeric materials such as but not limited to: TPE's (thermoplastic elastomers; TPU's (thermoplastic urethanes); elastomeric silicones (RTV, HTV, LSR, HCR) that are substantially both liquid impermeable and gas permeable (i.e., Breathable). For example, they may contain millions of micro-porosities per sq. cm. in their structure that are naturally formed during the mixing and molding process. In some examples, these elastomeric materials preferably would have a tear strength of 40 kN/m or even 50 kN/m or more, and preferably a tensile strength of 8-10 Mpa. Embodiments of these elastomeric materials would preferably have a Shore A hardness of 40 or even preferably 30 or even 20 Shore A hardness. Of course, other ranges may be used.

In some embodiments the elastomeric drape incorporates a built in set of internal channels into which can be inserted a flowable curing agent/material (for example, visible or UV light catalyzed) resin.

Examples of the light curable materials may include but are not limited to various blended mixtures of acrylate monomers, urethane acrylate oligomers, triacrylate cross linkers, plasticizers, and photo-initiators. Preferably this material is elastic and may have elongation properties of 10% or even 50% or possibly even 100% or more.

According to some embodiments, these incorporated visible or UV uncured resin filled channels (10, in FIG. 10) can be utilized to custom shape the oral drape device to a specific patient's anatomy and immobilize this shape over the target area after sequentially stretching different segments of the drape to their desired locations and then hardening the resin filled channels. In one example: The resultant three-dimensional form can be draped over varying topography (e.g., each patient's mouth is unique) of the gum ridge tissues surrounding the erupted teeth (e.g., after first being pulled over the erupted portions of the teeth in the dentulous situation), and then selectively patted and or stretched down over the gum ridge anatomy to achieve a high level of conformity to the individual gum ridge tissue topography. The incorporated light curable material can then be hardened around individual teeth and the gums around them by applying a readily available dental LED or UV light source to the material. In some examples the light curable materials may be selectively cured, for example by applying the light in a segmental manner to specific areas of the drape so as to immobilize the desired customized final shape of the drape to the target area.

In some embodiments, the manufacturing process herein described provides for using a stock sized pre-formed (molded) three dimensionally shaped drape device (e.g., that is non-custom made for a target anatomy) that can be readily and quickly adapted to each patient's specific anatomy to provide a "custom fit" to each patient's anatomy. Such a customized drape may provide a superior substantially semi-rigid barrier that can be used, for example, in the following applications:

The drape as described above may be used as a wound dressing or containment device (with or without impregnating the inner surface with a therapeutic) or as a delivery device itself (e.g., if an additional therapeutic agent is later impregnated on its inner surface as a coating in a later step of the manufacturing process) to hold and maintain a desired volume and concentration of the therapeutic in place onto the target area. Therapeutic applications include but are not limited to post-periodontal (gum) surgery, post-dental implant surgery, following deep debridement such as scaling and root planing (SRP) as part of a periodic periodontal STM (soft tissue management) regimen for chronic periodontitis patients.

In further embodiments, the initial form of the oral drape may substantially contain the treatment material in a more effective manner on the target treatment area, and allow for a significantly longer duration, larger quantity and optimal concentration and/or larger surface area application of the treatment material to the applied target area as compared to the known art. This may be advantageous to substantially prevent or limit saliva contamination (filled with pathogenic bacteria) and saliva washout (dilution of the therapeutic in the salivary fluid and its removal as is the case with the prior art).

According to some embodiments, the oral drape device may be placed over the teeth so as to expose the erupted portions of the teeth to the oral cavity (if present) and substantially cover the surrounding gums and or gum ridge after prior application (injecting) of a therapeutic treatment either onto the surface of the gum tissue, onto the tooth surface near the gum line, or into the natural (healthy or diseased) space (sulcus) between the gums and the teeth which often (i.e. prevalence rates of 50-70% in the adult population of industrialized nations) harbor pathogenic bacteria that cause gum disease (gingivitis and periodontitis). This improved exposure of the treatment material to the target treatment area may enable enhanced effectiveness in halting progression of the gum disease or aid in regeneration of healing tissue post-surgery that may reverse the disease state or promote healing of surgically incised tissue so as to bring the gums back to a state of health.

In further embodiments, if applied to the tooth structure near the gum line that may be partially covered by the oral drape, the treatment material may aid in more effectively re-mineralizing the demineralized (eroded) tooth structure that typically causes temperature (hot and cold) sensitivity to the teeth of patients who have these tooth erosions.

In accordance with further embodiments, a drape device that has been pre-impregnated on its inner surface with a treatment material at the time of fabrication or prior to insertion in the mouth, may have substantially all the advantages of the embodiments described above, while additionally enabling delivery of the therapeutic treatment material effectively and safely to a target location. In some examples this may obviate the need to first apply a treatment material onto or into the tissue to be treated. Such an embodiment may enhance the prevention and/or minimization of saliva contamination (filled with pathogenic bacteria) and saliva washout (dilution of the therapeutic in the salivary fluid and its removal).

As mentioned above, in some embodiments, the elastomeric materials used to form the pre-formed body structure of the oral draping device may be engineered to be differentially permeable (permeable to oxygen to permit "breathing" of the tissue under it and yet impermeable to fluids so as to prevent saliva contamination and washout).

In still further embodiments the oral drape device described herein may enable application to a patient anatomy to act as a barrier to prevent moisture contamination of the tooth structure by the surrounding soft tissues, thereby creating what is commonly known in the field of dentistry as a "dry field" (i.e. a substantially moisture-free work area), which is often a very important requirement for properly placing many dental restoratives (fillings etc.) into the teeth. In the currently described embodiment, application of the device may compliment and/or replace the typical rubber dam (typically a flat latex sheet drape), which is relatively cumbersome, time consuming to place (typically requires manually punching holes in it to cover the teeth, placement of a clamping device on one of the teeth to keep the rubber dam in place and often attachment of the rubber dam to an external frame to keep its otherwise loose unsupported sections away from the work area). The currently known rubber dam devices are typically uncomfortable for the patient and challenging for usage by the dentist for the above reasons.

In accordance with some embodiments, the oral drape device may be fabricated in full arch forms to cover all the teeth and surrounding gums of the upper or lower dental arches. It can also be fabricated to cover segments (e.g., anterior or posterior) or fabricated to cover a single tooth or only a few teeth and adjacent surrounding gum tissue.

In accordance with some embodiments, the oral drape device may be fabricated with a varying number of perforated or pre-configured cut out teeth holes as well as varying sizes and shapes for said perforated or pre-configured cut out teeth holes.

In additional embodiments, the drape device may be applied outside of the oral cavity, for example, by molding the material to a different shape (such as a sleeve or cuff), for covering a body part (e.g., the knee, elbow, ankle, neck etc.), by manually adapting so as to conform portions of the material to the surfaces of that body part so as to achieve excellent conformity and a "custom fit" of the material to that body surface, and then hardening at least some of the impregnated light curable material incorporated in its surfaces so as to achieve a semi-rigid cast or drape.

In further embodiments the drape device may also be formed in stock sized molded sections (e.g., to cover a limb, a portion of a limb, or a portion of the torso) and so may be used to treat a body area. In one example the drape device may be used to treat skin burn victims by effectively covering and partially immobilizing the damaged body parts substantially (especially in areas where there is normally joint movement of that body part), without the need for applying heavy plaster-type casts. In another example this application may be used where a treatment material may have first been applied separately to the damaged tissue or the treatment material may have been applied to the inner surface of the device prior to placing and adapting the device in a "custom fit manner to the desired treatment area".

In still further embodiments, the treatment material to be applied with the drape device may be formulated so that its therapeutic effect is in a time released manner or the treatment material may be first inserted into a manually or electronically controlled pumping device that has first been placed on the treatment area surface and then covered with the therapeutic draping device of the present invention.

The foregoing description of the embodiments of the invention has been presented for the purposes of illustration and description. It is not intended to be exhaustive or to limit the invention to the precise form disclosed. It should be appreciated by persons skilled in the art that many modifications, variations, substitutions, changes, and equivalents are possible in light of the above teaching. It is, therefore, to be understood that the appended claims are intended to cover all such modifications and changes as fall within the true spirit of the invention.

What is claimed is:

1. An anatomical drape for covering a treatment area of an anatomical part, the drape comprising:
   an elastomeric material capable of conforming to the contours of the anatomical part; and
   one or more internal channels containing uncured curing material; wherein the uncured curing material is adapted to be cured, thereby becoming hardened to at least partially set the drape in a configuration conforming to the anatomical part.

2. An anatomical drape as claimed in claim 1, wherein the elastomeric material of the drape is substantially liquid impermeable and gas permeable, both before and after curing of the curing material contained within the internal channels of the drape.

3. An anatomical drape as claimed in claim 1, wherein the drape is configured to generally conform to an oral anatomy.

4. An anatomical drape as claimed in claim 3, wherein the drape conforms to a gum ridge anatomy, wherein the drape forms an enclosed protective cover over the gum ridge with optional holes for passage of erupted teeth there through.

5. An anatomical drape as claimed in claim 3, wherein the drape conforms to a portion of the gum ridge anatomy, wherein the drape forms an enclosed protective cover over the gum ridge with optional holes for passage of erupted teeth there through.

6. An anatomical drape as claimed in claim 3, wherein the drape conforms to the gum ridge anatomy, wherein the drape forms an enclosed protective cover over the gum ridge with optional holes for passage of erupted teeth there through and substantially full coverage over portion of the gum ridge that are edentulous.

7. An anatomical drape as claimed in claim 1, wherein a curing material is distributed inside the internal channels to conform the drape to the anatomical structure covered by the drape.

8. An anatomical drape as claimed in claim 1, further comprising an external energy source usable to activate the curing material.

9. An anatomical drape as claimed in claim 8, wherein the energy source is one or more sources selected from the set including heat and/or light.

10. An anatomical drape as claimed in claim 7 wherein the curing material is a light curable agent selected from the group consisting of blended mixtures of oligomers, fillers and photo-initiators.

11. An anatomical drape as claimed in claim 1 wherein the drape can be stretched to the level of the gum line of each individual tooth on either its buccal or lingual/palatal aspects or stretched for a group of teeth and wherein the drape in its stretched form can be constrained to remain in its stretch form when the curing agent contained in the channels adjacent to the tooth or teeth is hardened.

12. An anatomical drape as claimed in claim 1 wherein one or more treatment material layers are included on at least one surface of the drape.

13. A kit of parts for covering a treatment area, the kit comprising one or more drapes according to claim 1, and a light source.

14. The kit of claim 13, further comprising one or more therapeutic sources.

15. The kit of claim 13, further comprising one or more treatment sources.

16. A method for the manufacture of an anatomical drape for covering a treatment area of an anatomical part, the method comprising the steps of:

(a) configuring a drape device by preparing a set of inserts that mirror the shape of internal channels and septum plugs of the drape device;

(b) molding elastomeric materials onto the set of inserts in order to produce a set of elastomeric spacers;

(c) inserting the set of inserts with spacers into a second mold;

(d) over-molding with similar elastomeric materials to create outer aspects of the elastomeric drape, (e) removing the set of inserts where the spacers remain to prepare a set of internal channels and self-sealing septum plugs inside the body of the drape; and (f) inserting one or more uncured curing material(s) through the set of self-sealing septum plugs into the internal channels of the drape so as to at least partially fill the internal channels with uncured curing materials.

17. A method according to claim 16, further comprising applying a second additive into the internal channels.

18. An oral drape for covering a treatment area of an oral cavity, the drape comprising an elastomeric material capable of conforming to the contours of the oral anatomical part and including a curing agent contained within internal channels distributed with in the drape wherein activation of the curing agent causes hardening of the material to at least partially set the drape in a configuration conforming to the anatomical part, the set drape being substantially gas permeable but liquid impermeable.

19. The oral drape of claim 18, where the drape is adapted to be applied and conformed to a gum ridge and to a mouthpiece that substantially covers the teeth and gum ridge or ridges, to provide for a continuous fluid seal of the mouthpiece treatment cavities to the drape(s).

\* \* \* \* \*